US012740692B2

(12) United States Patent
Birnkrant et al.

(10) Patent No.: US 12,740,692 B2
(45) Date of Patent: Sep. 22, 2026

(54) ENDOSCOPIC SYSTEM WITH ELECTRICAL BRIDGE IN DISTAL TIP

(71) Applicant: KARL STORZ Endovision, Inc., Charlton, MA (US)

(72) Inventors: Dashiell Birnkrant, Sutton, MA (US); Gerard Vadenais, Bellingham, MA (US); Katherine Rohena, Worcester, CA (US); Udaya Silva, Webster, MA (US)

(73) Assignee: KARL STORZ Endovision, Inc., Charlton, MA (US)

( * ) Notice: Subject to any disclaimer, the term of this patent is extended or adjusted under 35 U.S.C. 154(b) by 1042 days.

(21) Appl. No.: 17/946,204

(22) Filed: Sep. 16, 2022

(65) Prior Publication Data

US 2024/0090756 A1 Mar. 21, 2024

(51) Int. Cl.

*A61B 1/00* (2006.01)
*A61B 1/05* (2006.01)
*G02B 23/24* (2006.01)

(52) U.S. Cl.

CPC ............ *A61B 1/05* (2013.01); *A61B 1/00096* (2013.01); *G02B 23/2484* (2013.01)

(58) Field of Classification Search

CPC ......... A61B 1/05; A61B 1/00; A61B 1/00096; A61B 1/00124; A61B 1/051; A61B 1/0011; A61B 1/00126; A61B 1/053; A61B 1/042; G02B 23/2484; H04N 23/54; H05K 2201/10378

See application file for complete search history.

(56) References Cited

U.S. PATENT DOCUMENTS 11,211,513 B2 12/2021 Hermes et al.
2005/0270403 A1 12/2005 Adachi et al.
2007/0019952 A1* 1/2007 Fujimori ................ G03B 17/02 257/E31.118

(Continued)

OTHER PUBLICATIONS

Garret et al "Devices and Methods to Prevent Inadvertent Motion of Dynamically Rigidizing Apparatuses", Aug. 4, 2022, WO2022165302 A1 (Year: 2022).*

(Continued)

*Primary Examiner* — Sang H Nguyen
(74) *Attorney, Agent, or Firm* — David N. Villalpando; Jason Worgull; Jacqueline Cohen

(57) ABSTRACT

An electrical bridge connects to a packaged imaging sensor in the distal tip of a scope shaft. The bridge has an insulative body including a distal surface with a cross sectional size no greater than that of the packaged image sensor. A plurality of electrical contacts are arranged in an array along the distal surface of the insulative body for connecting to the packaged image sensor. Conductive paths are formed through the insulative body connecting to the electrical contacts. Wire attachment contacts connecting to the conductive paths. The wire attachment contacts are formed within the cross-sectional area of the insulative body and elongated in a longitudinal direction perpendicular the distal surface for soldering to wires oriented in the longitudinal direction. The wire attachment contacts are adjacent to respective voids in the insulative body for receiving the wires, the voids including insulative walls on two sides.

5 Claims, 7 Drawing Sheets

(56) References Cited

U.S. PATENT DOCUMENTS

| | | | | |
|---|---|---|---|---|
| 2007/0030334 | A1 | 2/2007 | Nishizawa | |
| 2007/0142711 | A1* | 6/2007 | Bayer | A61B 1/00101 600/172 |
| 2011/0013059 | A1 | 1/2011 | Nakamura et al. | |
| 2013/0284707 | A1* | 10/2013 | Kusakabe | B23K 1/005 219/85.13 |
| 2017/0105612 | A1 | 4/2017 | Wieters et al. | |
| 2017/0172388 | A1* | 6/2017 | Ohno | A61B 1/00124 |
| 2017/0265721 | A1* | 9/2017 | Ichimura | A61B 1/044 |
| 2018/0161903 | A1* | 6/2018 | Teraoka | H05K 13/0486 |
| 2019/0133423 | A1* | 5/2019 | Birnkrant | A61B 1/04 |
| 2020/0236775 | A1* | 7/2020 | Edlinger | H05K 3/3452 |
| 2021/0168276 | A1* | 6/2021 | Duckett, III | A61B 1/05 |
| 2021/0196110 | A1* | 7/2021 | Uram | A61B 1/07 |

OTHER PUBLICATIONS

Kennedy "Low Profile Circuit Board Connectors for Imaging Systems", Mar. 17, 2016, WO 2016040156 A1 (Year: 2016).*

Murata Manufacturing Co. Ltd., Technology guide: Neurostone, Promotional literature, c. 2021, pp. 1-7, Murata Manufacturing Co. Ltd., Japan.

Hirao T., S. Hamada, Novel Mult-Material 3-Dimensional Low-Temperature Co-Fired Ceramic Base, IEEEAccess, Jan. 14, 2019, pp. 1-5, Institute of Electrical and Electronics Engineers, New York.

* cited by examiner

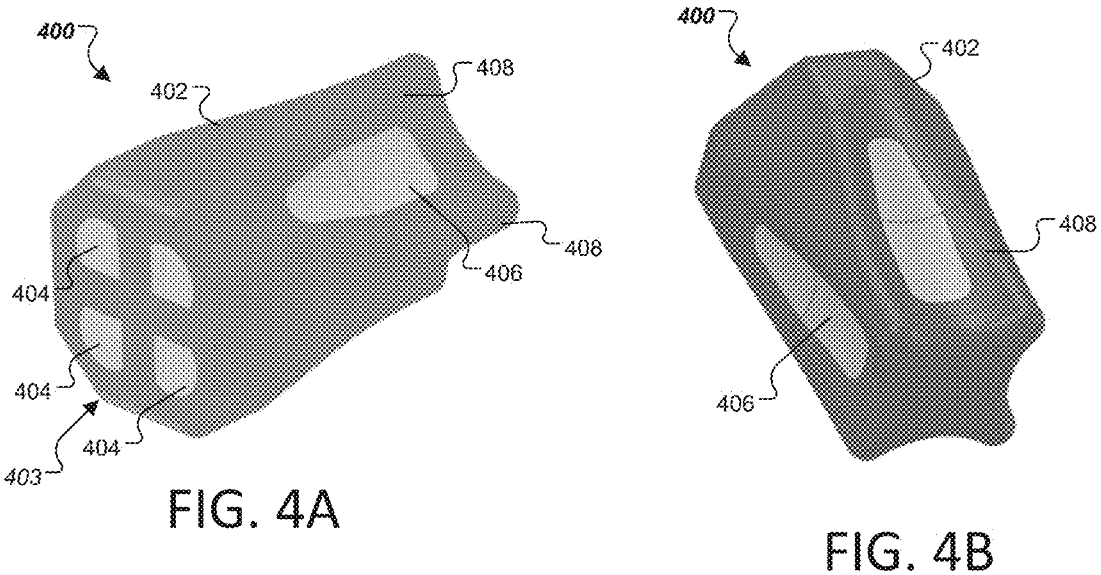
FIG. 4A
FIG. 4B
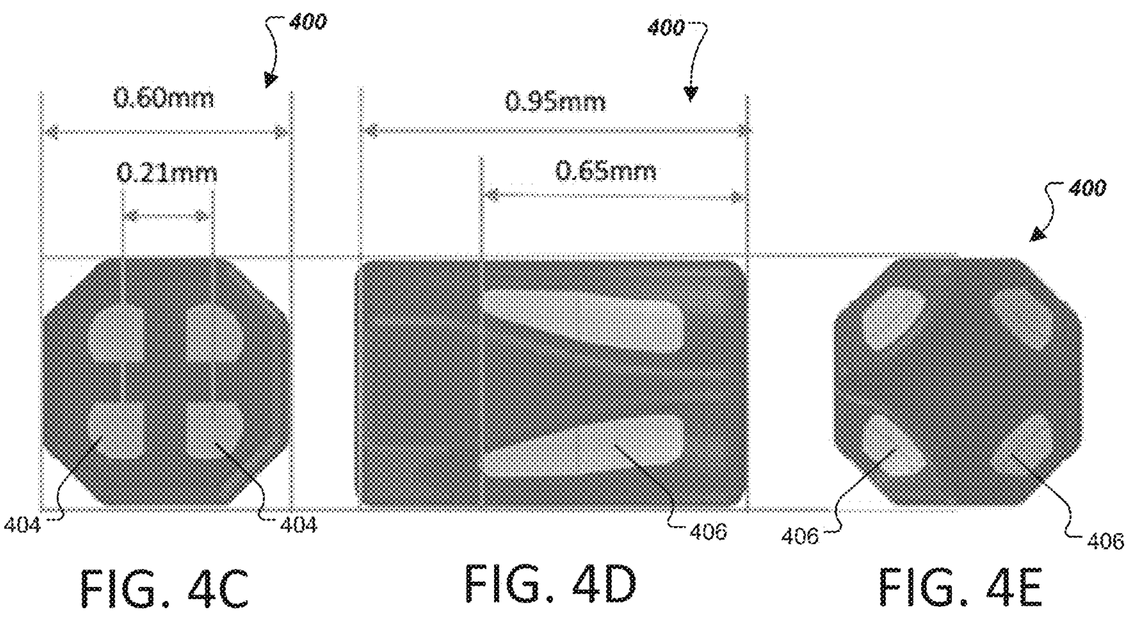
FIG. 4C
FIG. 4D
FIG. 4E

Light Source
8
Subject Scene
9
Light
10
Lens
11
16
Image Sensor (R, G, B)
14
Electrical Bridge
400
Supply Voltage
+
-
Analog Signal Processor
22
Timing Generator
26
Motion Sensors
27
A/D Converters
24
28
29
Image Processing Circuitry
30
Program Memory
54
System Memory
56
52
70
System Controller
50
Video Encoder
80
Display Controller
82
Image Display
88
User Inputs
64
Status Display
62
60
800

ENDOSCOPIC SYSTEM WITH ELECTRICAL BRIDGE IN DISTAL TIP

BACKGROUND OF THE INVENTION

Field of the Invention

This invention relates to video endoscopes, and in particular to endoscopes with very small, distally placed image sensors.

Description of the Background Art

The invention relates to optical instruments such as endoscopes and borescopes having an image sensor assembly at the distal end of the instrument shaft. Such instruments are used to visually inspect locations which are not readily accessible. For example, endoscopes are typically (although not exclusively) used in medical applications to provide a view of an area within a patient's body. Whether employed for medical, industrial, or other applications, the instrument typically includes an elongated shaft of relatively small diameter extending from a handle to a distal end.

An imaging arrangement is included with the instrument to allow a user to obtain a view from the shaft distal end. The imaging arrangement may include an electronic imaging device at the distal end of the instrument shaft. Such an electronic imaging device collects image data and communicates that data through the shaft and handle ultimately to a processing system that assembles the data to produce an image displayed on a suitable display device.

There remains a need in the art for ways to provide higher resolution capabilities for endoscopes, particularly in circumstances when a small bore diameter is desired. Further, there is a need for smaller and easier to assemble electrical assemblies for connecting to an imaging sensor at the tip of the scope shaft. In addition, there is a need for improved electrical connection structures to electrically connect a sensor in a small bore diameter shaft to the camera electronics without increasing the diameter of shaft distal tip beyond that needed to hold the sensor.

SUMMARY OF THE INVENTION

It is an object of the invention to provide for smaller and easier to produce electrical assemblies for the distal tip of an endoscope. It is also an object of the invention to provide an electrical bridge for easily assembling an endoscope, and methods of producing such an electrical bridge.

According to a first aspect of the invention, an electrical bridge is provided for connecting to a packaged imaging sensor with a cross-sectional size. The electrical bridge includes an insulative body including a distal surface with a cross sectional size no greater than that of the packaged image sensor. A plurality of electrical contacts are arranged along the distal surface of the insulative body in an array and adapted for connecting to a ball-grid array (BGA) of the packaged image sensor. A plurality of conductive paths are formed through the insulative body connecting to respective ones of the electrical contacts. A plurality of wire attachment contacts connect to respective ones of the conductive paths, the wire attachment contacts formed within a cross-sectional area of the insulative body and elongated in a longitudinal direction perpendicular the distal surface for soldering to wires oriented in the longitudinal direction. The wire attachment contacts are adjacent to respective voids in the insulative body for receiving the wires, the voids including insulative walls on two sides.

According to some implementations of the first aspect, the wire attachment contacts are elongated to a length at least 1.5 times a diameter of the electrical contacts.

According to some implementations of the first aspect, the body is composed of ceramic formed with 3D printing ceramic particles, the electrical contacts, conductive paths, and wire attachment contacts are composed of conductive metal formed by 3D printing conductive metal particles, and the voids are formed by 3D printing sacrificial particles. The electrical bridge may further be formed by curing the printed ceramic particles, conductive metal particles, and sacrificial particles with heat.

According to some implementations of the first aspect, the voids are at least partially open toward a circumference of the electrical bridge and the wire attachment contacts face outward toward the circumference of the electrical bridge from inner surfaces of the voids. The voids may be concave voids with the wire attachment contacts positioned along a central area of the concave voids. The concave voids may be progressively shallower toward a distal end of the electrical bridge.

According to some implementations of the first aspect, the invention also includes a cable assembly including the wires soldered to the wire attachment contacts and oriented in the longitudinal direction, wherein the wires do not extend beyond a cross-sectional area of the electrical bridge.

According to some implementations of the first aspect, there are four electrical contacts, four conductive paths, and four wire attachment contacts, and the four wire attachment contacts are separated equidistantly by respective intervening portions of the body, and the electrical contacts are positioned in a 2×2 array with a center-to-center spacing no more than 0.25 mm.

According to a second aspect of the invention, a method is provided for constructing an endoscope including an electrical bridge coupling an image processor to a packaged image sensor. The method includes providing an electrical bridge including a cross-sectional area no greater than that of the packaged image sensor, and including a plurality of electrical contacts arranged in an array on a distal face. The method includes placing the packaged image sensor in an elongated cradle fixture. The method includes placing the electrical bridge in the elongated cradle fixture with the plurality of electrical contacts in physical contact with a respective BGA contacts of the packaged image sensor. The method includes reflow soldering the BGA contacts of the packaged image sensor to the electrical contacts of the electrical bridge while they are both positioned in the elongated cradle fixture.

According to some implementations of the second aspect, the method includes reflow soldering the packaged image sensor to the electrical bridge further includes passing heated air through a plurality of voids formed in the elongated cradle fixture adjacent to the BGA contacts of the packaged image sensor to the electrical contacts of the electrical bridge.

According to some implementations of the second aspect, the method includes positioning a cable assembly with at least four tinned wires of the cable assembly contacting respective wire attachment contacts of the electrical bridge, and soldering the at least four tinned wires to the wire attachment contacts. The packaged image sensor and the cable assembly may be reflow soldered to the electrical bridge while reflow soldering the BGA contacts of the packaged image sensor to the electrical contacts of the electrical bridge.

According to some implementations of the second aspect, the elongated cradle fixture is formed of polyether ether ketone (PEEK).

According to some implementations of the second aspect, providing the electrical bridge includes 3D printing a bridge structure with a paste including ceramic particles, a paste including conductive metal particles, and a paste including sacrificial support particles, the bridge structure including: (a) a pre-formed insulative body including a distal surface with a cross sectional size no greater than that of the packaged image sensor; (b) a plurality of pre-formed electrical contacts disposed along the distal surface of the pre-formed insulative body; (c) a plurality of pre-formed conductive paths through the pre-formed insulative body connecting to respective ones of the pre-formed electrical contacts; and (d) a plurality of pre-formed wire attachment contacts connecting to respective ones of the pre-formed conductive paths, formed within the cross-sectional area of the pre-formed insulative body, and elongated in a longitudinal direction perpendicular the distal surface. The 3D printed bridge structure is fired to cure the insulative body, conductive paths, electrical contacts, and wire attachment contacts while burning away the sacrificial support particles to form the electrical bridge.

According to a third aspect of the invention, an optical instrument system is provided including an endoscopic instrument. The endoscopic instrument includes an instrument shaft including a distal end and a shaft interior. A packaged image sensor in the form of a BGA package including a cross-sectional size is positioned at the distal end of the instrument shaft at least partially in the shaft interior. A cable assembly extends along the shaft interior for coupling the packaged image sensor to a signal processor and supplying power and a clocking signal to the packaged image sensor. An electrical bridge electrically connects the cable assembly to the packaged image sensor. The electrical bridge includes an insulative body including a distal surface with a cross sectional size no greater than that of the packaged image sensor. A plurality of electrical contacts are arranged in an array along the distal surface of the insulative body and adapted for connecting to a BGA of the packaged image sensor. A plurality of conductive paths formed through the insulative body connecting to respective ones of the electrical contacts. A plurality of wire attachment contacts connect to respective ones of the conductive paths. The wire attachment contacts are formed within a cross-sectional area of the insulative body and elongated in a longitudinal direction perpendicular the distal surface for soldering to wires of the cable assembly oriented in the longitudinal direction. The wire attachment contacts are adjacent to respective voids in the insulative body for receiving the wires, the voids including insulative walls on two sides.

According to some implementations of the third aspect, the wire attachment contacts are elongated to a length at least 1.5 times a diameter of the electrical contacts.

According to some implementations of the third aspect, the voids are at least partially open toward a circumference of the bridge and the wire attachment contacts face outward toward the circumference of the electrical bridge from inner surfaces of the voids. The voids may be concave voids with the wire attachment contacts positioned along a central area of the concave voids. The concave voids may be progressively shallower toward a distal end of the electrical bridge.

According to some implementations of the third aspect, the wires of the cable assembly do not extend beyond a cross-sectional area of the electrical bridge along their connection to the electrical bridge.

These and other advantages and features of the invention will be apparent from the following description of representative embodiments considered along with the accompanying drawings.

BRIEF DESCRIPTION OF THE DRAWINGS

The present invention will become more fully understood from the detailed description given herein below and the accompanying drawings which are given by way of illustration only, and thus are not limitative of the present invention, and wherein:

FIGS. 4A-4E show various views of an electrical bridge according to an example embodiment of the invention;

DETAILED DESCRIPTION OF THE DRAWINGS

As used herein, elements (e.g., sensors and lenses) that are "optically arranged" in relation to other elements, refers to the elements' position along an optical path shared by the first and other elements. For example, a relay lens group optically arranged between an image sensor and an objective means that the relay lens group occupies a portion of the optical path that light travels from the objective to the image sensor for capturing images or video. "Optical image" is an image formed by the light rays from a self-luminous or an illuminated object that traverses an optical system or element.

Figure 1:
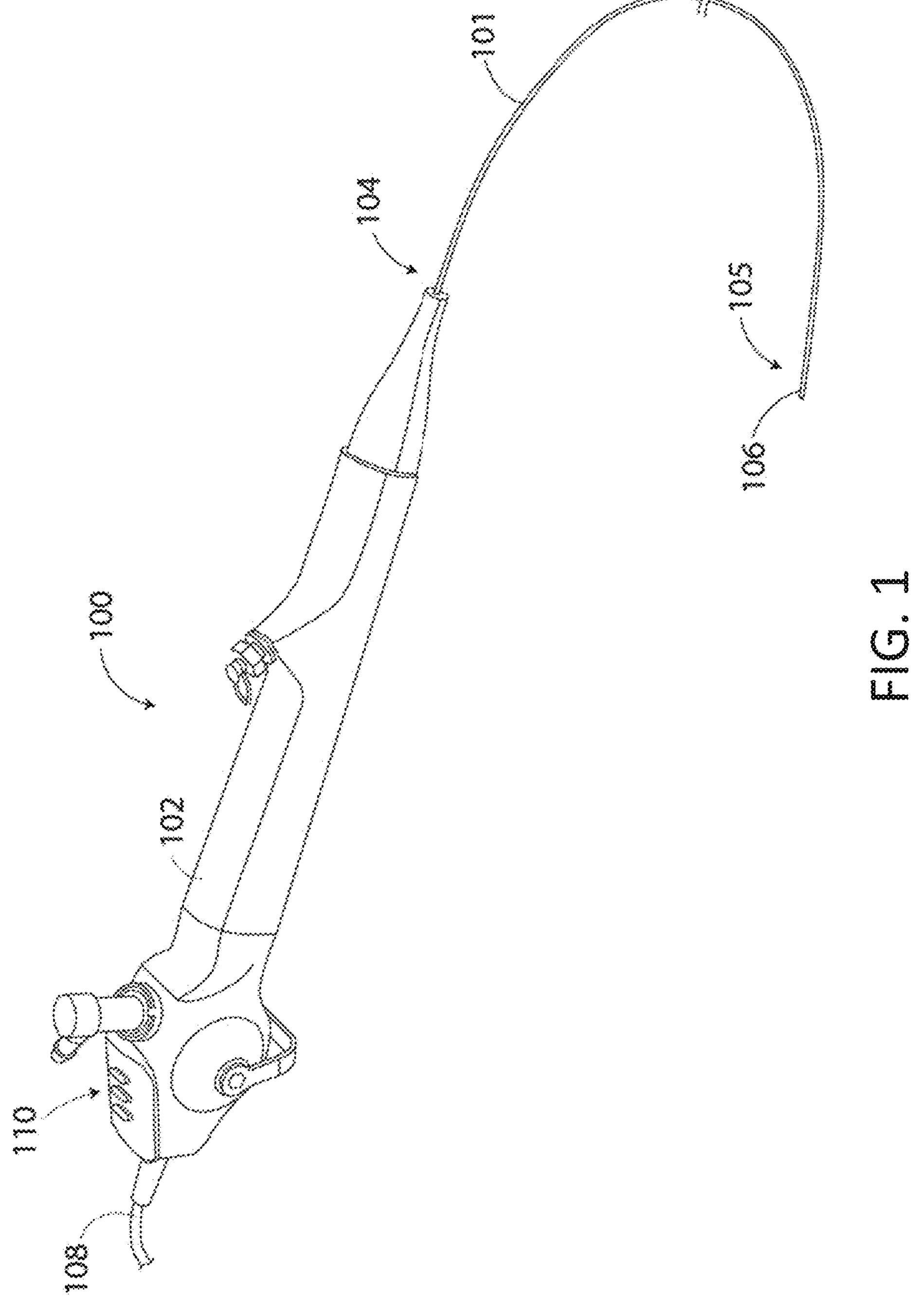
FIG. 1 is a perspective view of an endoscope instrument according to an example embodiment.

Referring to FIG. 1, depicted is a perspective view of an optical instrument 100 employing a distal tip sub-assembly according to one aspect of the present invention. Optical instrument 100 includes an elongated shaft 101 and a handle 102. Shaft 101 extends from a proximal end shown generally at reference numeral 104 connected to handle 102 to a distal end generally indicated at reference numeral 105. A distal end portion 106 is included at the shaft distal end 105. The image sensors according to the present invention are located in distal end portion 106, although it is not shown in FIG. 1 due to the scale of the figure. The depicted shaft 101 is a flexible implementation, but rigid-shaft implementations are also possible.

Optical instrument 100 receives electrical operating power through a cable 108 which extends from a proximal end of handle 102 in this example instrument. This power may be used to operate one or more light sources and other electronic elements mounted within distal end portion 106, including multiple electronic image sensors. Also, data signals from such an imaging device may be communicated through appropriate conduits within shaft 101 and handle 102 to cable 108. These data signals may be communicated through cable 108 to processing equipment (not shown) which processes the image data and drives one or more video monitors to display the images collected at distal end 105 of optical instrument 100. Those familiar with endoscopes and borescopes will appreciate that optical instrument 100 includes a number of additional features such as controls 110 for controlling the operation of the instrument. Although data transmission relating to the image sensors will be described further below, the general operation and control of optical instrument 100 will not be described further herein in order to avoid obscuring the present invention in unnecessary detail.

Figure 2:
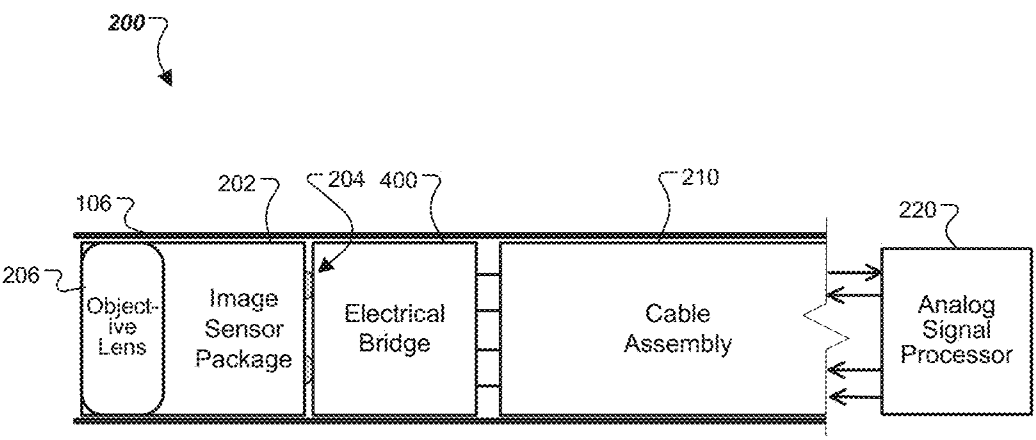
FIG. 2 is a cross section block diagram of a distal end of an instrument shaft according to an example embodiment of the invention.

FIG. 2 is a cross section block diagram of a portion of an optical instrument system 200 including a distal end portion 106 of an instrument shaft. Positioned in the distal end portion 106 is an electrical sub-assembly including a packaged image sensor 202, an electrical bridge 400, and a cable assembly 210. Cable assembly 210 electrically couples packaged image sensor 202 to an analog signal processor 220, which, in this embodiment, is positioned in the handle of host endoscope.

Packaged image sensor 202 in an example implementation is an ultra-small image sensor such as the OVM6948 CameraCubeChip™ sensor made by OmniVision. This example packaged image sensor measures 0.65 mm×0.65 mm, with a height of 1.158 mm. As shown, packaged image sensor 202 includes an objective lens 206 integrated in the package, and a 2×2 array of ball-grid array (BGA) contacts 204 along the bottom of the sensor's package. While a packaged image sensor with an integrated objective lens is used in this embodiment, other embodiments may instead use an external objective lens, positioned similarly in the distal end portion 106.

Electrical bridge 400 is generally an insulative connector for carrying packaged image sensor 202 and electrically connecting it to cable assembly 210. Electrical bridge 400, as shown in more detail in FIGS. 4A-4C, generally includes an insulative body and a set of electrical contacts 404 arranged along distal surface of the insulative body and adapted for connecting to a BGA of the packaged image sensor by soldering. A set of conductive paths formed through the insulative body connect to respective ones of the electrical contacts. A plurality of wire attachment contacts are provided for soldering to wires from cable assembly 210, oriented in the longitudinal direction. As further described below, the use of an electrical bridge rather than a printed circuit board (PCB) or a socket type connector allows the entire sub-assembly to have a cross sectional area no greater than that of packaged image sensor 202, allowing for the smallest possible shaft 101 (or distal end portion 106) to be used for a particular image sensor, while avoiding difficulties typically associated with electrically connecting to a packaged image sensor in such a small volume.

Cable assembly 210, in this implementation, includes 4 wires enclosed in an insulative sheath, and may include multiple layers of insulation or shielding enclosing the four wires, which are individually insulated as well.

Figure 3:
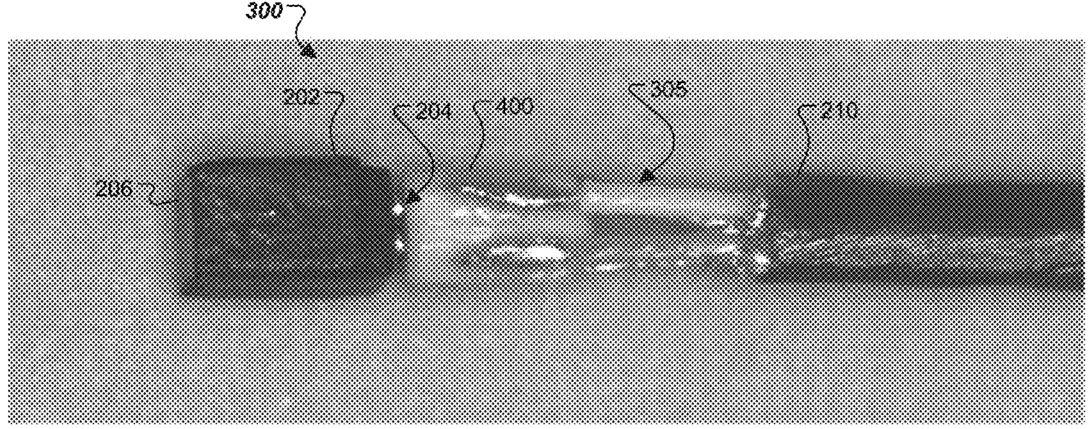
FIG. 3 shows a photograph of a subassembly including a packaged image sensor, an electrical bridge, and a cable assembly according to an example embodiment of the invention.

FIG. 3 shows a photograph of a subassembly 300 including a packaged image sensor 202, an electrical bridge 400, and a cable assembly 210 according to an example embodiment of the invention. As can be seen, subassembly 300 is constructed such that electrical bridge 400 and cable assembly 210 have a cross sectional area no larger than packaged image sensor 202. In this implementation, four wires 305 are separated by trimming back the outer insulation of cable assembly 210, and soldered to electrical bridge 400. In particular, along the solder connection of wires 305 to electrical bridge 400, the cross-sectional size of the entire assembly does not extend past that of packaged image sensor 202, allowing the entire assembly to fit within any scope shaft diameter into which packaged image sensor 202 can be inserted.

FIGS. 4A-4E show various views of an electrical bridge 400 according to an example embodiment of the invention. FIG. 4A shows a perspective view of the distal end of electrical bridge 400. FIG. 4B shows a perspective view of the proximal end. FIG. 4C shows an end view of the distal end. FIG. 4D shows a size view. FIG. 4E shows an end view of the proximal end.

Referring to FIGS. 4A-4E, an electrical bridge 400 includes an insulative body 402, including a distal surface 403 with a cross sectional size no greater than that of the packaged image sensor. Four electrical contacts 404 are arranged along the distal surface of the insulative body, disposed in an array adapted for connecting to a BGA of the packaged image sensor. While four electrical contacts 404 are used in this implementation in a 2×2 array, other implementations may use more or fewer electrical contacts corresponding, generally, to the number of BGA contacts on the corresponding image sensor. For example, an array of 2×3, 3×3, 3×4, or larger may be used in some implementations.

Four conductive paths are formed through insulative body 402 connecting each of the electrical contacts 404, to its respective wire attachment contact 406. Wire attachment contacts 406 are formed within the cross-sectional area of insulative body 402 and elongated in a longitudinal direction perpendicular distal surface 403 of insulative body 402 for soldering to wires oriented in the longitudinal direction. In this implementation, wire attachment contacts 406 are adjacent to respective voids in insulative body 402 for receiving the wires. The voids are formed by insulative walls 408 on two sides of wire attachment contacts 406. The voids are at least partially open toward a circumference of electrical bridge 400, and wire attachment contacts 406 face outward toward the circumference of electrical bridge 400 from inner surfaces of the voids. In this implementation, the voids are concave voids with the wire attachment contacts positioned along a central area of the concave voids. The concave voids are progressively shallower toward a distal end of the electrical bridge. In other implementations, the voids may have another shape.

Wire attachment contacts 406 are preferably elongated to a length at least 1.5 times a diameter of electrical contacts 404, and preferably at least two or three times the diameter of the electrical contacts 404. Such an elongated shape provides a much more reliable and easily manufacturable electrical connection than soldering wires directly to the BGA contacts of the packaged image sensor.

In this implementation, there are four electrical contacts 404, four conductive paths, and four wire attachment contacts 406. Wire attachment contacts 406 are separated equidistantly by respective intervening portions of insulative body 402. As depicted in FIG. 4C, electrical contacts 404 are positioned in a 2×2 array with a center-to-center spacing of 0.21 mm in order to match the BGA pitch of the packaged image sensor for which electrical bridge 400 is designed. Other BGA pitches may be used. In this implementation, the cross sectional size of electrical bridge 400 is 0.6 mm, and the length is 0.95 mm, providing a cross-sectional size smaller than that of the target packed image sensor which is a 0.65 mm square cross section.

Figure 5:
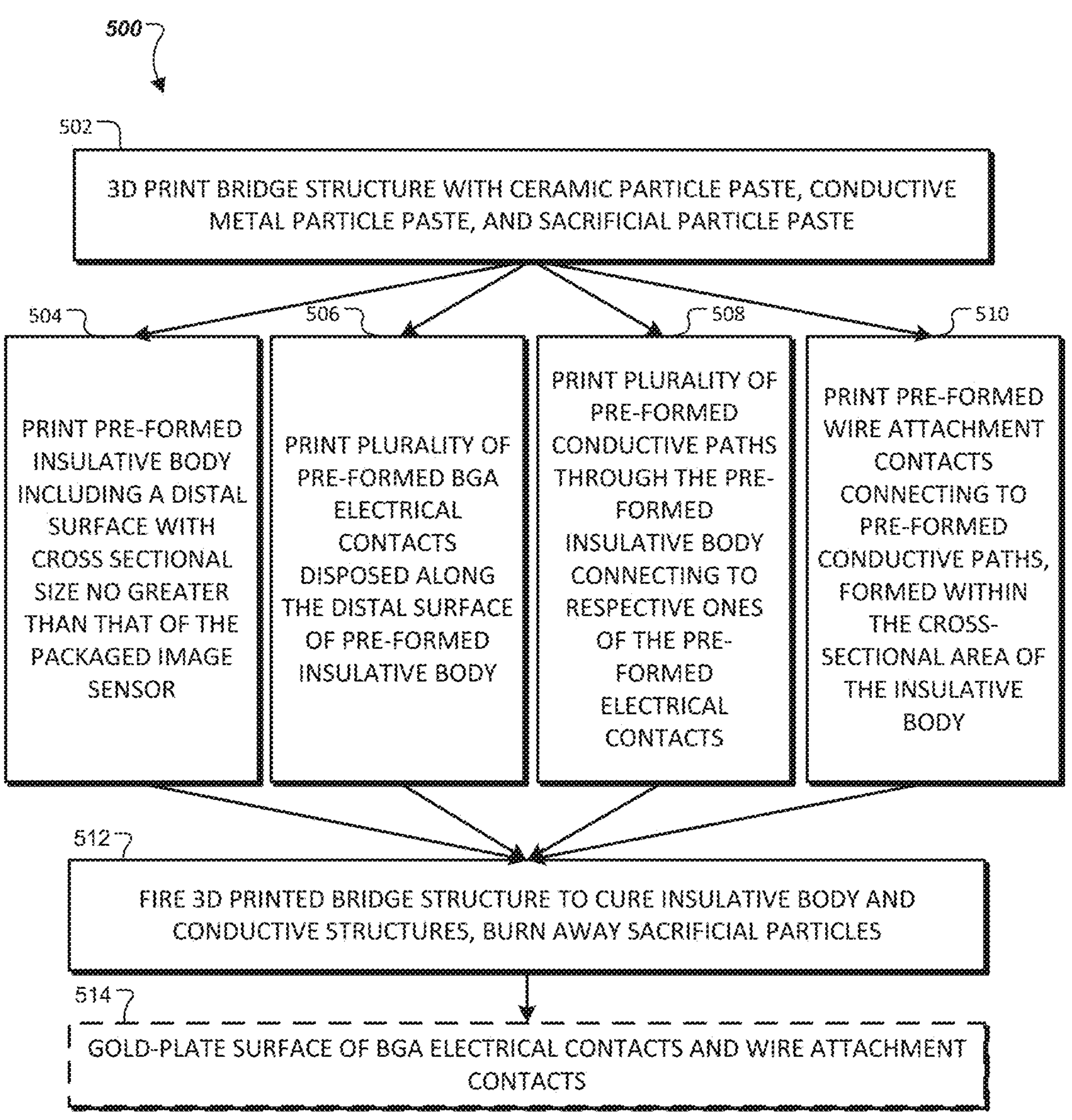
FIG. 5 is a flow diagram of a process for manufacturing an electrical bridge according to some embodiments of the invention.

FIG. 5 shows a flow diagram 500 of a process for manufacturing an electrical bridge according to some embodiments of the invention. Generally, an electrical bridge such as that of FIG. 4 is formed in preferred implementations by 3D printing. The process begins at block 502, that includes 3D printing a bridge structure with a paste including ceramic particles, a paste including conductive metal particles, and a paste including sacrificial support particles. In some implementations, sacrificial support particles are not used, depending on the shape and position of voids in the desired final structure. The 3D printed bridge structure includes a pre-formed insulative body including a distal surface with a cross sectional size no greater than that of the packaged image sensor, which is printed as shown at block 504. It also includes a plurality of pre-formed electrical contacts disposed along the distal surface of the pre-formed insulative body, which is 3D printed in parallel with block 504 as shown at block 506. It also includes a plurality of pre-formed conductive paths through the pre-formed insulative body connecting to respective ones of the pre-formed electrical contacts, which are printed as shown at block 508. Finally, the 3D printed bridge structure includes a plurality of pre-formed wire attachment contacts connecting to respective ones of the pre-formed conductive paths, formed within the cross-sectional area of the insulative body, and elongated in a longitudinal direction perpendicular the distal surface, which are printed at block 510 during the same printing process.

Next, at block 512, the process includes firing the 3D printed bridge structure to cure the insulative body, conductive paths, electrical contacts, and wire attachment contacts while burning away any sacrificial support particles to form the electrical bridge. The electrical contacts and wire attachment contacts may also be gold-plated, as shown at block 514.

In some embodiments, the 3D printing and manufacturing employs the additive manufacturing process known as Neurostone™ provided by Murata Manufacturing Co., Ltd. Other suitable ceramic 3D printing processes may be used in other embodiments.

Figures 6A, 6B, 6C:
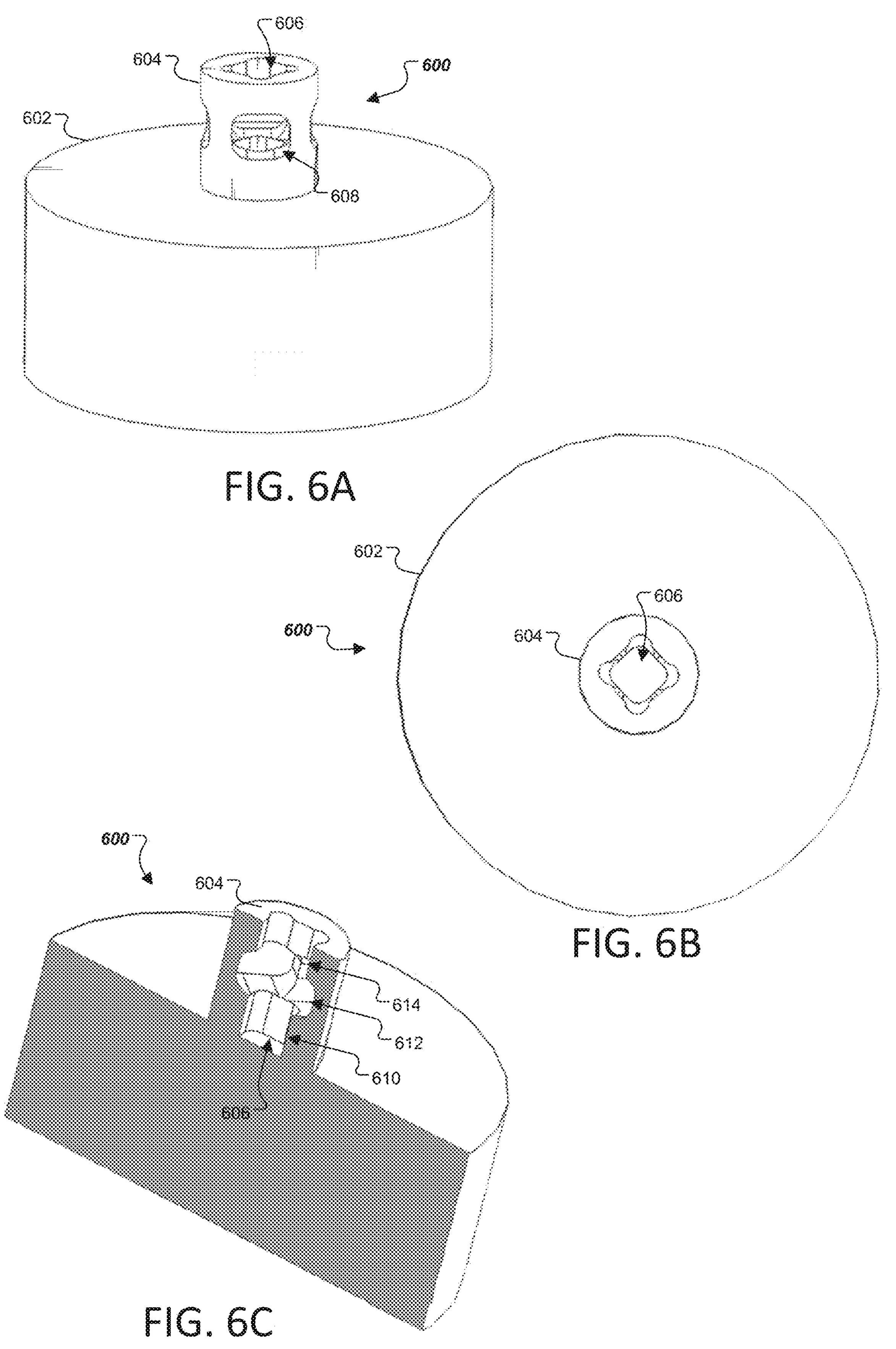
FIG. 6A shows a perspective view of an elongated cradle fixture used in assembling the sub-assembly of FIG. 3 according to some embodiments of the invention.
FIG. 6B shows a top view of the elongated cradle fixture of FIG. 6A.
FIG. 6C shows a cross-section view of the elongated cradle fixture of FIG. 6A.

FIG. 6A shows a perspective view of an elongated cradle fixture 600 used in assembling the sub-assembly of FIG. 3 according to some embodiments of the invention. FIG. 6B shows a top view of the elongated cradle fixture 600 of FIG. 6A. FIG. 6C shows a cross-section view of the elongated cradle fixture 600 of FIG. 6A. Referring to FIGS. 6A-6C, cradle fixture 600 includes a supporting body 602 and a cradle 604. In this implementation, cradle fixture 600 is formed of polyether ether ketone (PEEK). In other implementations, cradle fixture 600 may be formed of another suitable structure with good heat insulative properties, preferably a hard machinable plastic or 3D printed plastic. Ceramics may also be used.

Supporting body 602 is generally for holding cradle 604 and may be of any suitable size and shape. Cradle 604 has an interior void 606, in this embodiment formed by machining a solid piece of PEEK. Void 606 has four apertures 608 allowing airflow to the interior of void 606 for reflow soldering when cradle fixture 600 holds a packaged image sensor 202 and electrical bridge 400. As seen in FIG. 6C, void 606 includes a lower portion 610 shaped to hold a packaged image sensor 202 in place, which is positioned in the cradle fixture 600 with the BGA facing upward.

Above lower portion 610 is an airflow region 612 through which heated air can flow during reflow soldering. As seen in the cross-section view, airflow region 612 is wider than lower portion 610 and open to apertures 608. Above airflow region 612 is an upper portion 614 shaped to hold electrical bridge 400. The corners of upper portion 614 are enlarged to allow increased airflow along the surfaces of electrical bridge 400. An assembly process using cradle fixture 600 is shown in FIG. 7.

Figure 7:
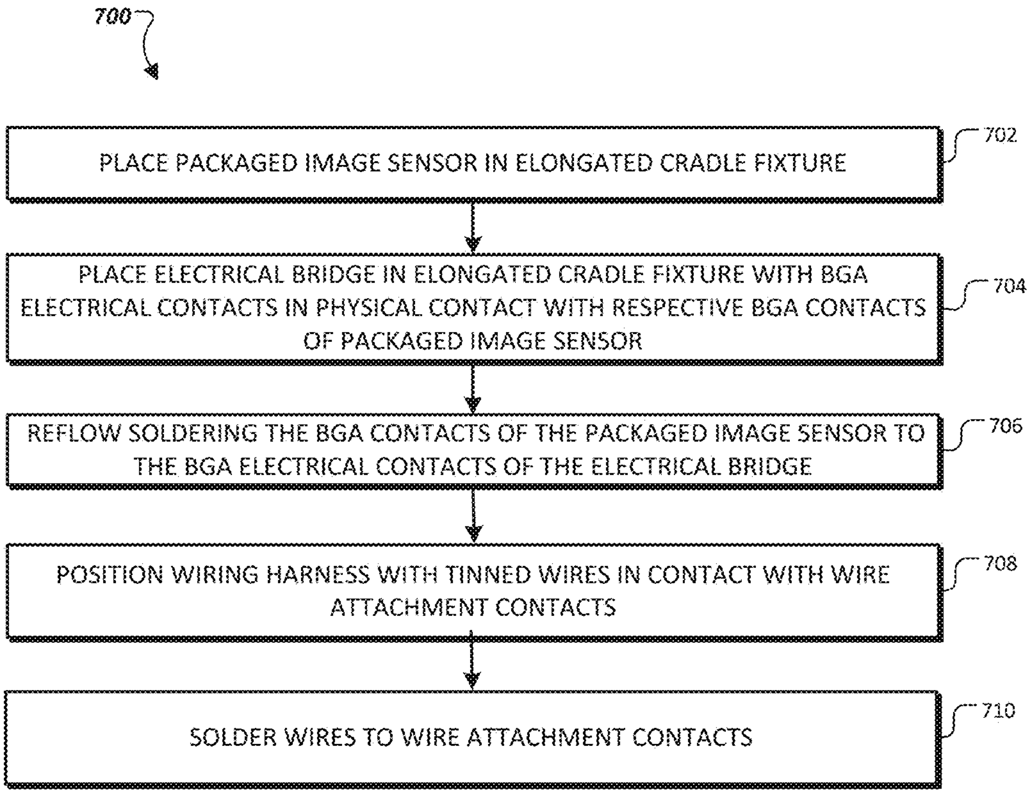
FIG. 7 is a flow diagram of a process for manufacturing the subassembly of FIG. 3 according to some embodiments of the invention.

FIG. 7 shows a flow diagram 700 of a process for manufacturing the subassembly of FIG. 3 according to some embodiments of the invention. The process begins at block 702 where packaged image sensor 202 is placed in cradle fixture 600. This is done by inserting it into void 606 with the sensor end oriented downward and BGA oriented upward. Placement may be done by hand or with a suction type pick-and-place head.

Then at block 704, electrical bridge 400 is positioned in cradle fixture 600 with the electrical contacts (404) in physical contact with the respective BGA contacts of the packaged image sensor. Preferably, void 606 is sized to hold each piece in place such that no further mechanical stabilization is required. At this point in the process, the apertures 608 are adjacent to the BGA contacts to be soldered.

At block 706, cradle fixture 600 is placed into a reflow oven and a reflow soldering step is performed to reflow solder the BGA contacts (204, FIG. 3) to the opposing electrical contacts 404 of electrical bridge 400. Because the difficulty of establishing reliable electrical connection due to the small size and spacing of the BGA contacts, and excess solder will tend to cause solder to run between contacts and form short circuit paths, solder paste is preferably not used. During reflow soldering, the heated air is able to flow into apertures 608, and around airflow region 612, and between packaged image sensor 202 and electrical bridge 400 to heat BGA contacts 204. Air may also flow upward through the enlarged corners of upper portion 614.

At block 708, a prepared cable assembly 210 (FIG. 3) with insulation and wires stripped as shown in FIG. 3, and wire ends tinned with solder, is positioned with the tinned wires in contact with wire attachment contacts 406 (FIG. 4). At block 710, the tinned wires are soldered to wire attachment contacts 406. In some embodiments, block 710 is performed following block 706 with hand soldering. In some embodiments, block 710 is performed in parallel with block 706 with reflow soldering.

The depicted process assembles the sub-assembly of FIG. 3 in a reliable and high-yield process, avoiding short circuits and open circuits as is common when hand soldering together such a small sub-assembly. The sub-assembly may then be inserted into a scope shaft for assembling the completed optical instrument.

Figure 8:
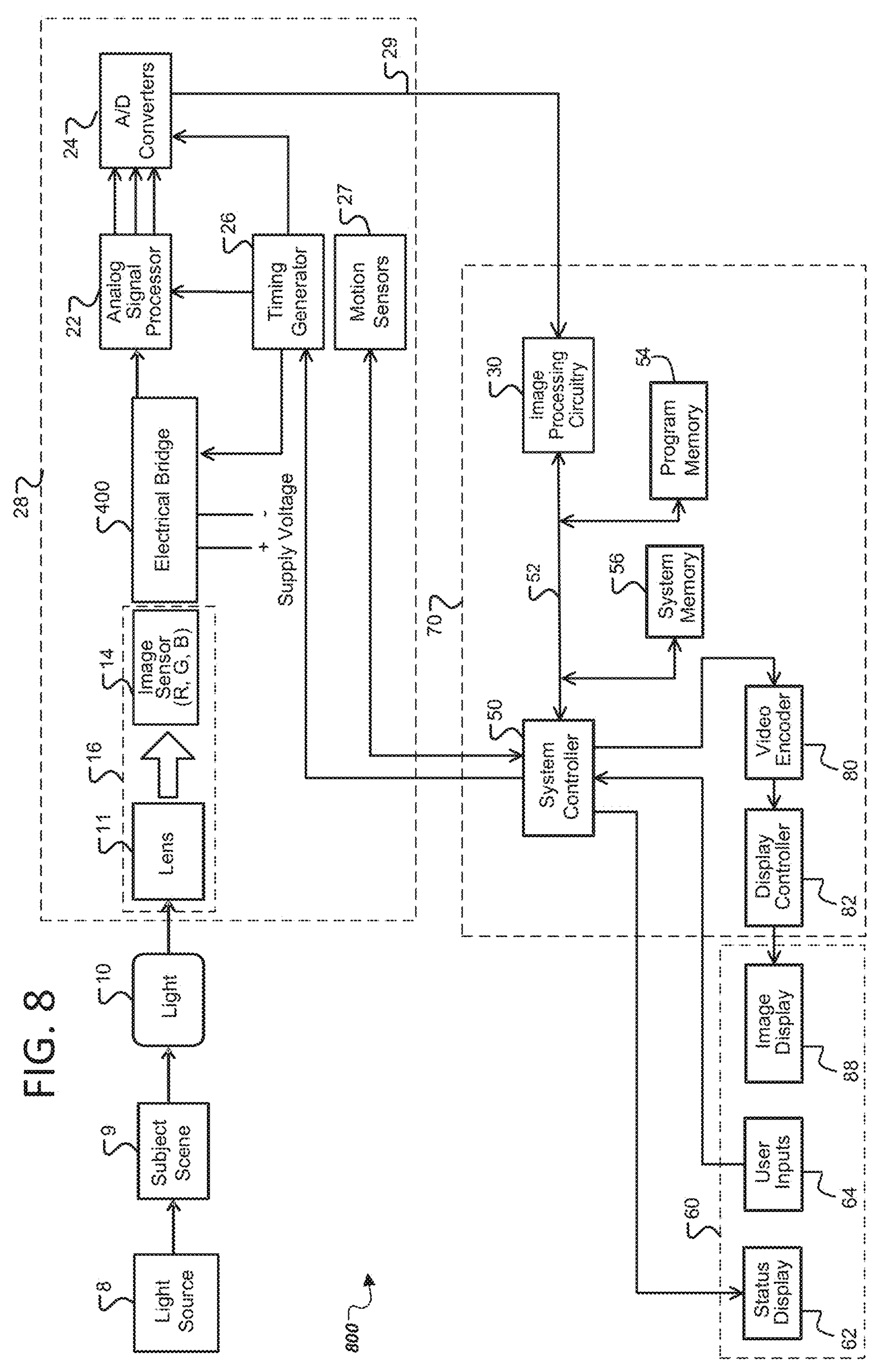
FIG. 8 is a block diagram of an optical instrument system according to some embodiments of the invention.

FIG. 8 shows is a block diagram of an optical instrument system 800 according to an example embodiment of the present invention. While this example circuit is shown for an endoscope, the present invention is applicable to more than one type of medical scope instrument, but typically is most applicable for ultra-small imaging scope applications for the smallest parts of the anatomy. Such imaging systems employ image capture at the instrument distal tip.

A light source 8 illuminates subject scene 9 and light 10 reflected from (or, alternatively, as in the case of certain fluorescent or digital microscope arrangements, transmitted or emitted by) the subject scene forms an optical image via lens 11, where the light is focused, and passed toward the image sensor. Lens 11 may be an objective lens 206 integrated in a package 16 with a packaged image sensor (such as packaged image sensor 202, FIG. 2), or may be a separate objective lens installed distal to the packaged image sensor 14.

Optical instrument system 800, in this embodiment, is a single-channel imaging system in which a camera 28 employs image sensor 14 to convert the incident light to an electrical signal by, for example, integrating charge for each picture element (pixel). Image sensor 14 may be active-pixel type complementary metal oxide semiconductor sensors (CMOS APS) or a charge-coupled devices (CCD), to give just two possible examples. CMOS sensors are used for the preferred ultra-small embodiments. The output analog signal from image sensor 14, passed through electrical bridge 400, is processed by analog signal processor 22 and applied to analog-to-digital (A/D) converter 24 for digitizing the analog sensor signals. In some versions (typically CMOS designs), the analog signal processing and A/D converters may be integrated into the image sensor 14 module. Electrical bridge 400 also connects image sensor 14 to positive and negative supply voltage rails to provide a sensor supply voltage.

The system's camera 28 generally includes timing generator 26, which produces various clocking signals to select rows and pixels and synchronizes the operation of image sensor 14, analog signal processor 22, and A/D converter 24. One or more motion sensors 27 such as, for example, an accelerometer, gyro, or magnetometer, may be mounted in the endoscope shaft, tip, or handle to aid in detecting movement, including rotation, of the endoscope. Image sensor 14 is preferably an ultra-small image sensor such as that of FIG. 2. A scope distal tip electronic assembly houses image sensor 14, with electrical coupling of signals and a supply voltage accomplished through electrical bridge 400 and cable assembly 210. The locations of each of analog signal processor 22, the A/D converter 24, and the timing generator 26 may vary, for example in the scope handle 102 or partially integrated into the distal tip electronic assembly. The functional elements of the camera 28 may be fabricated as a single integrated circuit as is commonly done with CMOS image sensors or they may be separately-fabricated integrated circuits.

A system controller 50 controls the overall operation of the image capture device based on a software program stored in program memory 54. This memory can also be used to store user setting selections and other data to be preserved when the camera 28 is turned off. Data connection 29 carries the digital image data of image sensor 14 to image processing circuitry 30, which may be integrated with system controller 50 in some versions or may be a separate programmable logic device or data processor. A data bus 52 provides a pathway for address, data, and control signals. In some variations, data bus 52 may also carry data connection 29.

Image processing circuitry 30 performs image processing operations as needed for the particular imaging application. Processed image data are continuously sent to video encoder 80 to produce a video signal. This signal is processed by display controller 82 and presented on image display 88. This display is typically an HD, UHD, or 4K format liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 may manage the graphical user interface (GUI) presented on one or more of the displays (e.g., on image display 88). The GUI typically includes menus for making various option selections.

Image processing circuitry 30, system controller 50, system and program memories 56 and 54, video encoder 80, and display controller 82 may be housed within camera control unit (CCU) 70. CCU 70 may be responsible for powering and controlling light source 8 and/or camera 28. As used herein "CCU" refers to units or modules that power, receive data from, manipulate data from, transmit data to, and/or forwards data from optical instrument cameras. CCU functionalities may be spread over multiple units known as, for example, a "connect module", "link module", or "head module".

Those skilled in the art will appreciate that the electronic components and power/data cable may be connected to or included with the image sensor sub-assembly in a variety of fashions. For example, the power/data connections of cable assembly 210 (FIG. 2) may include a detachable plug for connecting to the scope handle to provide a replaceable scope shaft or may be integrated permanently with the scope.

Because digital cameras employing endoscopic instruments and related circuitry for signal capture, processing, and correction and for exposure control are well-known, the above description is directed in particular to elements forming part of, or cooperating more directly with, a method and apparatus in accordance with the present invention. Elements not specifically shown or described herein are selected from those known in the art. Certain aspects of the embodiments may be provided in software. Given the system as shown and described according to the invention in the following materials, software not specifically shown, described or suggested herein that is useful for implementation of the invention is conventional and within the ordinary skill in such arts.

The invention being thus described, it will be obvious that the same may be varied in many ways. Such variations are not to be regarded as a departure from the scope of the invention, and all such modifications as would be obvious to one skilled in the art are intended to be included within the scope of the following claims. For example, reference to an endoscope is intended merely as a representative example application and is not intended to be limiting. Implementations include optical scopes such as exoscopes and borescopes.

Further still, although this distribution of imaging device functional control among multiple programmable logic devices, programmable logic devices, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

The invention claimed is:

1. A method of constructing an endoscope including an electrical bridge structure coupling an image processor to a packaged image sensor, the method comprising:

providing an electrical bridge structure including a cross-sectional area no greater than that of the packaged image sensor, and including a plurality of electrical contacts on a distal face arranged in an array, wherein the step of providing an electrical bridge structure includes 3D printing the bridge structure with a paste comprising ceramic particles, a paste comprising conductive metal particles, and a paste comprising sacrificial support particles, the bridge structure comprising: (a) a pre-formed insulative body including a distal surface with a cross sectional size no greater than that of the packaged image sensor; (b) a plurality of pre-formed electrical contacts disposed along the distal surface of the pre-formed insulative body; (c) a plurality of pre-formed conductive paths through the pre-formed insulative body connecting to respective ones of the pre-formed electrical contacts; and (d) a plurality of pre-formed wire attachment contacts connecting to respective ones of the pre-formed conductive paths, formed within the cross-sectional area of the pre-formed insulative body, and elongated in a longitudinal direction perpendicular the distal surface, and firing the 3D printed bridge structure to cure the insulative body, conductive paths, electrical contacts, and wire attachment contacts while burning away the sacrificial support particles to form the electrical bridge;

placing the packaged image sensor in an elongated cradle fixture;

placing the electrical bridge structure in the elongated cradle fixture with the plurality of electrical contacts in physical contact with a respective BGA contacts of the packaged image sensor; and reflow soldering the BGA contacts of the packaged image sensor to the electrical contacts of the electrical bridge structure while they are both positioned in the elongated cradle fixture.

2. The method of claim 1, wherein:

reflow soldering the packaged image sensor to the electrical bridge structure further comprises passing heated air through a plurality of voids formed in the elongated cradle fixture adjacent to the BGA contacts of the packaged image sensor to the electrical contacts of the electrical bridge.

3. The method of claim 1, further comprising:

positioning a cable assembly with at least four tinned wires of the cable assembly contacting respective wire attachment contacts of the electrical bridge structure; and soldering the at least four tinned wires to the wire attachment contacts.

4. The method of claim 3, wherein:

the packaged image sensor and the cable assembly are reflow soldered to the electrical bridge structure while reflow soldering the BGA contacts of the packaged image sensor to the electrical contacts of the electrical bridge.

5. The method of claim 1, wherein:

the elongated cradle fixture is formed of polyether ether ketone (PEEK).

* * * * *